(12) United States Patent
Rimbault et al.

(10) Patent No.: US 10,427,955 B2
(45) Date of Patent: Oct. 1, 2019

(54) IRRADIATION CHAMBER FOR LIQUID PURIFICATION APPARATUS, PURIFICATION APPARATUS AND BEVERAGE DISPENSER

(71) Applicant: NESTEC S.A., Vevey (CH)

(72) Inventors: Celine Rimbault, Vittel (FR); Renaud Sublet, Vittel (FR)

(73) Assignee: Societe des Produits Nestle S.A., Vevey (CH)

( * ) Notice: Subject to any disclaimer, the term of this patent is extended or adjusted under 35 U.S.C. 154(b) by 206 days.

(21) Appl. No.: 15/327,194

(22) PCT Filed: Jul. 9, 2015

(86) PCT No.: PCT/EP2015/065725
§ 371 (c)(1),
(2) Date: Jan. 18, 2017

(87) PCT Pub. No.: WO2016/008803
PCT Pub. Date: Jan. 21, 2016

(65) Prior Publication Data
US 2017/0158529 A1 Jun. 8, 2017

(30) Foreign Application Priority Data
Jul. 18, 2014 (EP) .................................. 14177691

(51) Int. Cl.
*C02F 1/32* (2006.01)
*A61L 2/10* (2006.01)
(Continued)

(52) U.S. Cl.
CPC ................ *C02F 1/325* (2013.01); *A61L 2/10* (2013.01); *A61L 9/20* (2013.01); *C02F 1/008* (2013.01);
(Continued)

(58) Field of Classification Search
CPC .. C02F 1/325; C02F 1/008; C02F 2201/3222; C02F 2201/3224; C02F 2201/3227;
(Continued)

(56) References Cited

U.S. PATENT DOCUMENTS

| 4,323,810 A | 4/1982 | Horstmann |
| 5,124,131 A | 6/1992 | Wekhof |

(Continued)

FOREIGN PATENT DOCUMENTS

| CA | 2393593 | 1/2004 |
| WO | 2009108045 | 9/2009 |

*Primary Examiner* — Xiuyu Tai
(74) *Attorney, Agent, or Firm* — K&L Gates LLP (57) ABSTRACT

The invention relates to an irradiation chamber (300) for a liquid purification apparatus using ultraviolet light irradiation against the reproduction of pathogenic microorganisms, comprising an inlet portion (302), an outlet portion (303), and a main portion (301) having an elongated shape, the irradiation chamber (300) having an internal surface defining an cavity, the irradiation chamber (300) being provided with ultraviolet light emitting means configured to irradiate liquid in the irradiation chamber (300) with ultraviolet light, the main portion (301) having a shape enlarged compared to the inlet portion (302). The internal surface of the irradiation chamber (300) defining the cavity is a three dimensional rounded surface, having no edge which forms a recess. The invention also relates to a liquid purification apparatus and to a beverage dispenser.

20 Claims, 4 Drawing Sheets

(51) Int. Cl.
*A61L 9/20* (2006.01)
*C02F 1/00* (2006.01)

(52) U.S. Cl.
CPC ............... *C02F 2201/326* (2013.01); *C02F 2201/3222* (2013.01); *C02F 2201/3224* (2013.01); *C02F 2201/3227* (2013.01); *C02F 2303/04* (2013.01); *C02F 2307/10* (2013.01)

(58) Field of Classification Search
CPC ............ C02F 2201/326; C02F 2303/04; C02F 2307/10; C02F 2201/3228; A61L 2/10; A61L 9/20; B01J 19/123; F15D 1/02; F24F 2013/088
See application file for complete search history.

(56) References Cited

U.S. PATENT DOCUMENTS

| | | | |
|---|---|---|---|
| 2002/0030011 A1 | 3/2002 | Constantine et al. | |
| 2004/0011414 A1* | 1/2004 | Ueberall | C02F 1/325 138/39 |
| 2004/0226893 A1 | 11/2004 | Kamimura et al. | |
| 2012/0261319 A1* | 10/2012 | Shinagawa | C02F 1/001 210/170.03 |

* cited by examiner

IRRADIATION CHAMBER FOR LIQUID PURIFICATION APPARATUS, PURIFICATION APPARATUS AND BEVERAGE DISPENSER

CROSS REFERENCE TO RELATED APPLICATIONS

The present application is a National Stage of International Application No. PCT/EP2015/065725, filed on Jul. 9, 2015, which claims priority to European Patent Application No. 14177691.4, filed Jul. 18, 2014, the entire contents of which are being incorporated herein by reference.

FIELD OF THE INVENTION

The invention relates to an irradiation chamber for a liquid purification apparatus, using ultraviolet irradiation against the reproduction of pathogenic microorganisms. In particular, the invention relates to an irradiation chamber for a small liquid purification apparatus and to a beverage dispenser comprising such a liquid purification apparatus, for example a water fountain.

BACKGROUND OF THE INVENTION

The present invention relates generally to liquid purification apparatuses comprising an irradiation chamber for liquid purification. The present invention also relates to a beverage dispenser comprising such a purification apparatus.

One of the most essential tasks in purifying liquids such as water for drinking is disinfection, so as to ensure that any pathogenic microorganisms (e.g. bacteria, viruses, and protozoans) present in the water cannot cause illness in anyone who drinks it. It is known to perform this disinfection by the process of ultraviolet (UV) irradiation, where a volume of water being treated is bombarded with high-energy radiation in the form of UV light. The UV light damages the DNA and RNA of the pathogenic microorganisms, destroying their ability to reproduce and effectively neutralizing their ability to cause disease.

Since such systems use light to disinfect, their effectiveness is reduced on liquid which is not naturally clear or which has not been filtered to remove suspended solids. The scope of "purification," for the purposes of this document, should thus be understood as encompassing the disinfection of liquid in which turbidity is minimal.

Traditional UV liquid purification systems have employed gas-discharge lamps as UV sources, in particular mercury-vapor lamps. Recently, it has become more and more common to employ ultraviolet light-emitting diodes (UV-LEDs) as a source of ultraviolet light for irradiation. UV-LEDs have numerous advantageous aspects which makes them appealing for use in an ultraviolet liquid purification system, notably their compact size, robustness, and lack of toxic components such as the mercury vapor found in conventional lamps. The solid-state nature of UV-LEDs also enables them to be switched on and off instantly, a further advantage relative to conventional gas-discharge lamps.

There are several examples in the prior art of UV-LEDs being employed to purify a liquid by ultraviolet irradiation. For example, the document CN 202175579 describes an irradiation device in which a single tube is spiraled around an array of UV-LEDs, and the document KR 20110007554 describes a faucet with a built-in UV-LED sterilizer for treating the liquid issuing from it. In addition, the document KR 20040073732 describes a system for purifying water that is drawn from a reservoir and conducted through a sterilizer directly to a nozzle for dispensing.

In a general manner, to ensure an efficient purification of the treated liquid, said liquid has to be irradiated by ultraviolet for a sufficient time. The known purification apparatuses commonly comprise an irradiation chamber where the liquid is irradiated. Thanks to the volume provided in this irradiation chamber, the corresponding volume of liquid may be irradiated and purified, making this volume of purified liquid immediately available. The volume of the irradiation chamber also reduces the average velocity of the liquid flowing in the irradiation chamber, thus enhancing the residence time of the liquid in said chamber, and so the irradiation time.

Typical irradiation chambers have substantially the shape of a cylinder, closed at each end by a straight wall.

The applicant has found that, in classical irradiation chamber, many dead volumes exist. "Dead volumes" are parts of the chamber where the fluid stagnates, even when a fluid stream is established in the irradiation chamber. Such dead volumes should be avoided because they reduce the effective volume of the chamber: when part of the liquid stagnates, the remaining part of the liquid in the irradiation chamber flows quicker than it would without dead volumes. Dead volumes also promote the formation of inorganic deposits in the irradiation chamber.

The applicant has also found that dead volumes generally exist around the inlet in the irradiation chamber. Thus, the liquid entering the irradiation chamber is not efficiently treated as soon as it enters the chamber, i.e. from said inlet in the irradiation chamber.

In small purification apparatuses such as those employed in water fountains, the irradiation chamber has a relatively small volume (e.g. 100 mL to 200 mL). Dead volumes are a problem particularly acute in such small irradiation chambers, because any loss in the volume actually available and used for treating the liquid should be avoided, or else, in order to obtain a certain minimum irradiation time of all the liquid flowing out of the irradiation chamber, the volume of the chamber must be increased and/or the flow rate decreased. It is not possible to wait for the fluid present in the chamber to be naturally mixed and homogenized, because generally the quantity of liquid to be delivered compared to the volume of the irradiation chamber imposes a significant continuous flow in the irradiation chamber.

Adding a mixer, which creates a turbulent flow, may be contemplated. However, using a mixer is not efficient in all reactor shapes and may have other drawbacks. For example, a power supply may be required, or this may increase the maintenance needs. Using a line having no enlarged irradiation chamber (i.e. the irradiation is performed in a portion of the hose forming the line) may be contemplated, but this is not possible in most applications because of the irradiation time required for disinfection. Placing baffles inside the irradiation chamber may also be contemplated. But the baffles create corners in the irradiation chamber which may favour the development of microorganisms and biofilm formation.

It is therefore an objective of the present invention to provide an irradiation chamber for a liquid purification apparatus using ultraviolet irradiation that solves or reduces at least one of the above mentioned drawbacks.

SUMMARY OF THE INVENTION

In a first aspect of the invention there is provided an irradiation chamber for a liquid purification apparatus using ultraviolet light irradiation against the reproduction of pathogenic microorganisms, comprising an inlet portion, an outlet portion, and a main portion having an elongated shape, the irradiation chamber having an internal surface defining a cavity, the irradiation chamber being provided with ultraviolet light emitting means configured to irradiate liquid in the irradiation chamber with ultraviolet light, the main portion having an enlarged shape compared to the inlet portion. The internal surface of the irradiation chamber defining the cavity is a three dimensional rounded surface, having no edge which forms a recess.

The smoothly rounded surface defining the irradiation chamber reduces the dead volumes in said chamber. All or almost all the volume of the chamber is used for the purification of the liquid which flows in said chamber.

In an embodiment of the invention, the internal surface of the irradiation chamber defining the cavity is a surface of revolution whose generatrix is a portion of a curve having no cusp all along said portion of the curve. In other word, the mathematical function which defines generatrix of this surface of revolution is differentiable all along the part of the curve defining the surface.

The main portion of the irradiation chamber may be connected to the inlet and outlet portions by smoothly curved connecting portions. The main portion may in particular comprise a cylindrical part. In this case, the connecting portions may be composed of curved surfaces each having a curvature radius greater than or equal to the radius of the cylindrical part. In particular, the connecting portions are composed of curved surfaces each having a curvature radius greater than or equal to 0.5 cm.

In an embodiment, the main portion of the irradiation chamber may have a length between 5 and 15 cm inclusive. The main portion of the irradiation chamber may have an internal constant cross section having a surface between 0.5 $cm^2$ and 4 $cm^2$ inclusive.

Typically, the volume of the main portion of the irradiation chamber may be 200 mL or less, and preferably around 100 mL.

In a configuration of the invention, the outlet portion is collinear to the inlet portion. In another configuration, the outlet portion is substantially orthogonal with the inlet portion.

The ultraviolet light emitting means may comprise ultraviolet light emitting diodes. Alternatively, the ultraviolet light emitting means may comprise optical fiber portions which are connected to at least one ultraviolet light source and which are configured to transmit ultraviolet light from said at least one source into the irradiation chamber.

The invention also relates to a purification apparatus comprising an irradiation chamber as previously described. The invention finally relates to a beverage dispenser such as a water fountain comprising such a liquid purification apparatus, configured to purify the beverage before delivery by ultraviolet irradiation.

BRIEF DESCRIPTION OF THE DRAWINGS

Additional features and advantages of the present invention are described in, and will be apparent from, the description of the presently preferred embodiments which are set out below with reference to the drawings in which.

DETAILED DESCRIPTION OF THE INVENTION

For a complete understanding of the present invention and the advantages thereof, reference is made to the following detailed description of the invention.

The invention is further described with reference to the following examples. It will be appreciated that the invention as claimed is not intended to be limited in any way by these examples.

It should also be appreciated that various embodiments of the present invention can be combined with other embodiments of the invention and are merely illustrative of the specific ways to make and use the invention and do not limit the scope of the invention when taken into consideration with the claims and the following detailed description.

Figure 1:
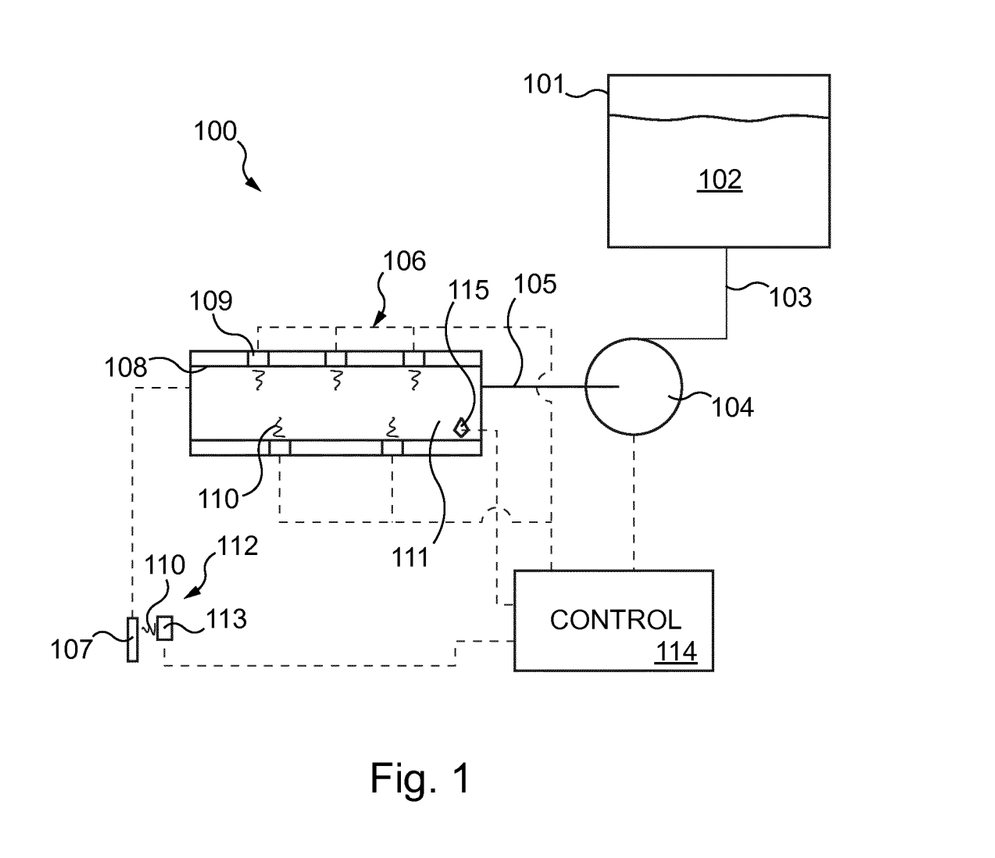
FIG. 1 is a schematic depiction of an example of liquid purification apparatus comprising an irradiation chamber.

FIG. 1 is a schematic depiction of a liquid purification apparatus 100, in particular a purification apparatus comprised in a beverage dispenser such as a water fountain. The following description of a liquid purification apparatus relates to the general architecture of an example of liquid purification apparatus using ultraviolet irradiation. This general description may relate to both an apparatus as known in the state of the art and an apparatus according to an embodiment of the invention, as the present invention relates in particular to the irradiation chamber used in such a purification apparatus and does not change the general architecture of such an apparatus.

The liquid purification apparatus 100 is provided a reservoir 101 which contains a volume of liquid 102. In this embodiment the liquid 102 is water, but may optionally be any liquid of sufficient transparency. The liquid 102 is drawn from the reservoir 101 through the pump tube 103 and into the pump 104. From the pump 104, the liquid 102 is conducted into the circulation tube 105.

The circulation tube 105 extends from the pump 104 through the primary irradiation device 106, as shown, establishing fluid communication between the pump 104 and the discharge port 107 of the purification apparatus.

In the primary irradiation device 106, the liquid is purified by UV irradiation. In the represented embodiment, the irradiation device 106 comprises a tubular structure, with an internal surface 108. The internal surface 108 is reflective, being fabricated preferably from a highly-polished metal or alternately covered with a reflective metal foil. A plurality of primary ultraviolet light-emitting diodes (UV-LEDs) 109 is provided upon the interior surface 108 of said primary irradiation device 106 so that they project the ultraviolet radiation 110 inside an irradiation chamber 111.

The irradiation chamber is described in detail with reference to FIGS. 2 to 4.

After having been irradiated and thus disinfected in the irradiation chamber 111, the liquid 102 flows to the discharge port 107 and is discharged from the apparatus 100.

Optionally, the purification apparatus may be further provided with a secondary irradiation device 112 comprising at least one secondary UV-LED 113. The secondary irradiation device 112 projects ultraviolet rays 110 on the discharge port 107, for sterilizing the discharged fluid.

The output and number of UV-LEDs 109, 113 disposed in the primary and secondary irradiation devices 106 and 112 may vary according to the particular characteristics of the apparatus 100 and the application in which it is to be employed.

In the represented embodiment, the apparatus 100 further comprises a control means 114, which is configured to electrically control the operation of the primary and secondary irradiation means 106 and 112 and the pump 104. Preferably, the control means 114 also communicates with a photosensor 115 disposed within the primary irradiation device 106. The control means 114 uses the output of the photosensor 115 to calibrate the intensity of the ultraviolet radiation 110 emitted from the primary UV-LEDs 109, as well as to monitor the operation of the apparatus 100 and warn the user of any malfunctions.

While the apparatus discussed herein employs a photosensor 115, it should be understood that an apparatus 100 may be configured with other sensors (e.g. flow meters, water clarity sensors, thermocouples, etc.) which communicate with the control means 114 and which permit it to continually adjust the parameters of the operation of the liquid purification means. The exact configuration and program of operation of the control means 114 will thus vary according to the application in which the liquid purification device is to be employed.

FIGS. 2A, 2B, 3A and 3B are schematic representations of irradiation chambers for small purification apparatuses, and more particularly representation of the cavity defined by the internal surface of the irradiation chambers. The represented purification chambers may correspond to the purification chamber 111 of a purification apparatus as represented in FIG. 1. Of course, such purification chambers may be used in various types of apparatuses and applications, not limited to beverage dispensers.

Figure 2A:
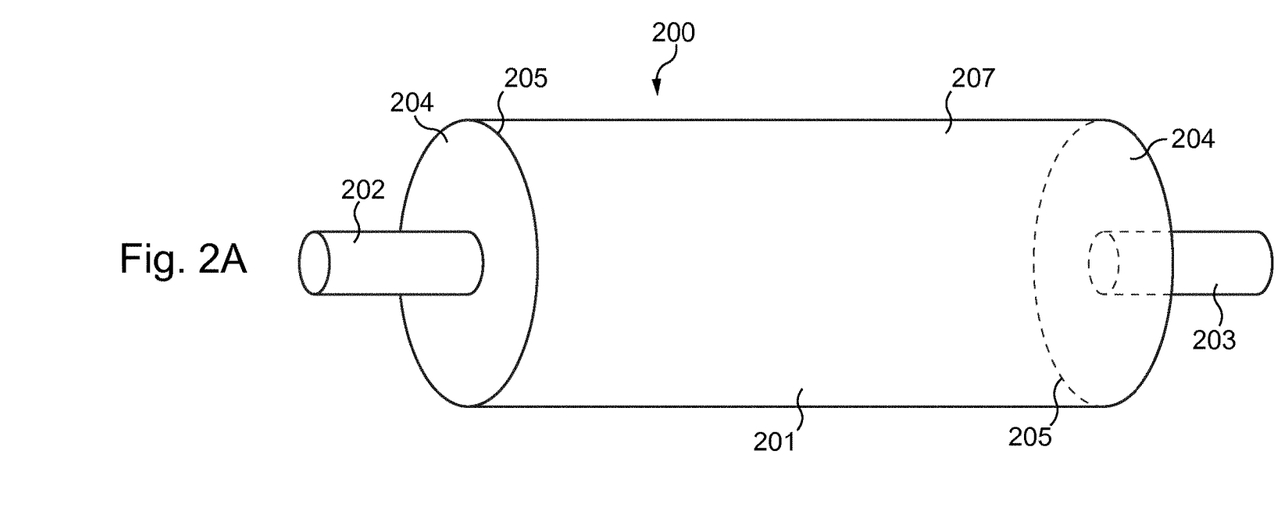
FIG. 2A is a schematic representation of an irradiation chamber for a small purification apparatus, said irradiation chamber having the design generally implemented in the state of the art.

The purification chamber 200 represented in FIG. 2A has a typical design according to the state of the art. The purification chamber 200 comprises a main portion 201, an inlet portion 202 and an outlet portion 203.

The main portion 201 (and more specifically its internal surface) has the shape of a cylinder with closed end. The ends of the cylinder forming the main portion 201 are closed by straight walls 204. The inlet portion 202 and the outlet portion 203 are connected to the walls 204.

At each end of the main portion 201, the walls form a recess or corner 205 inside the main portion, at the periphery of said main portion end.

In the corner 205, inorganic deposit may occur. In addition, dead volumes 206 are created in the corners 205. Dead volumes correspond to parts of the chamber where the fluid stagnates, or flows very slowly compared to the average fluid velocity in the irradiation chamber.

Figure 2B:
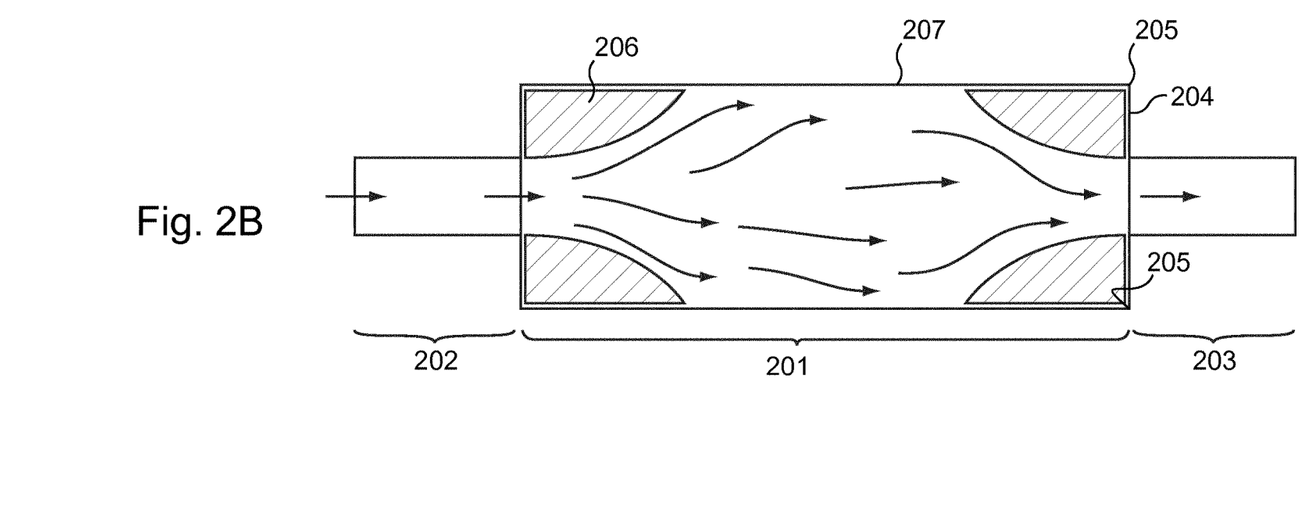
FIG. 2B is a schematic representation of a section of the irradiation chamber of FIG. 1, in which the streamlines of a liquid flowing in the irradiation chamber are schematically represented.

FIG. 2B illustrates this phenomenon. FIG. 2B is a representation of a section of the irradiation chamber of FIG. 1. The streamlines of a liquid flowing in the irradiation chamber 200 from the inlet portion 202 to the outlet portion 203 are schematically represented by arrows. The represented flow is only illustrative, but shows that the dead volumes 206 (hatched in FIG. 3) exist in particular around the inlet and the outlet of the main portion 201, in the corner formed between the walls 204 and the cylindrical wall 207 of the main portion 201. As a liquid flowing from the inlet portion 202 to the outlet portion 203 does not circulate in the dead volumes, the efficient volume of the chamber used to slow the liquid and ensure a sufficient residence time in the irradiation chamber (in particular in the main portion 201) is reduced compared to the geometrical (whole) volume of the chamber. Dead volumes also promote formation of inorganic deposit in the irradiation chamber.

In particular, dead volumes 206 generally exist around the inlet in the main portion 201 of the irradiation chamber. Thus, a liquid entering in the main part 201 is not efficiently treated as soon as it enters.

Figure 3A:
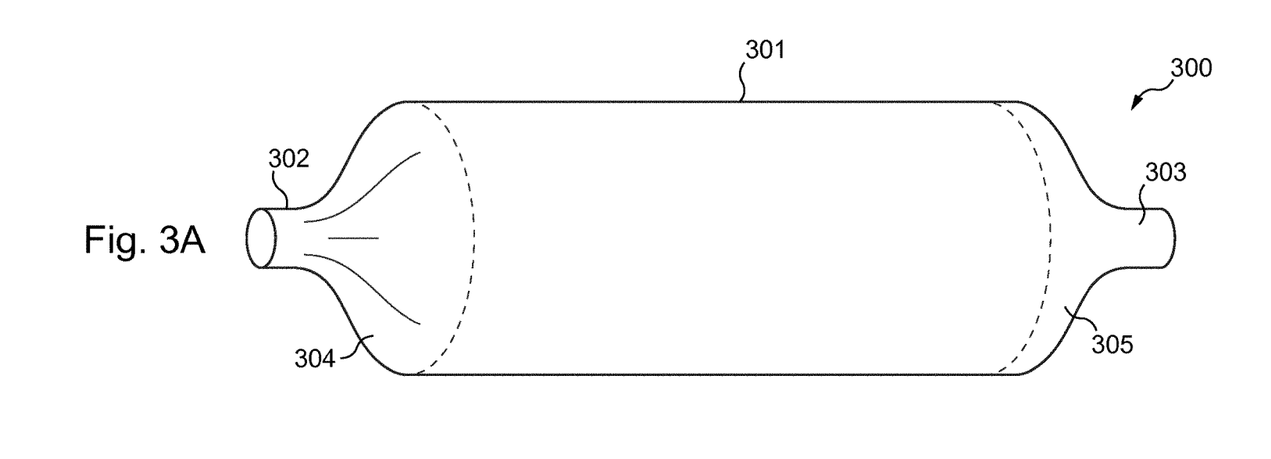
FIG. 3A is a schematic representation of an irradiation chamber according to an embodiment of the invention.
Figure 3B:
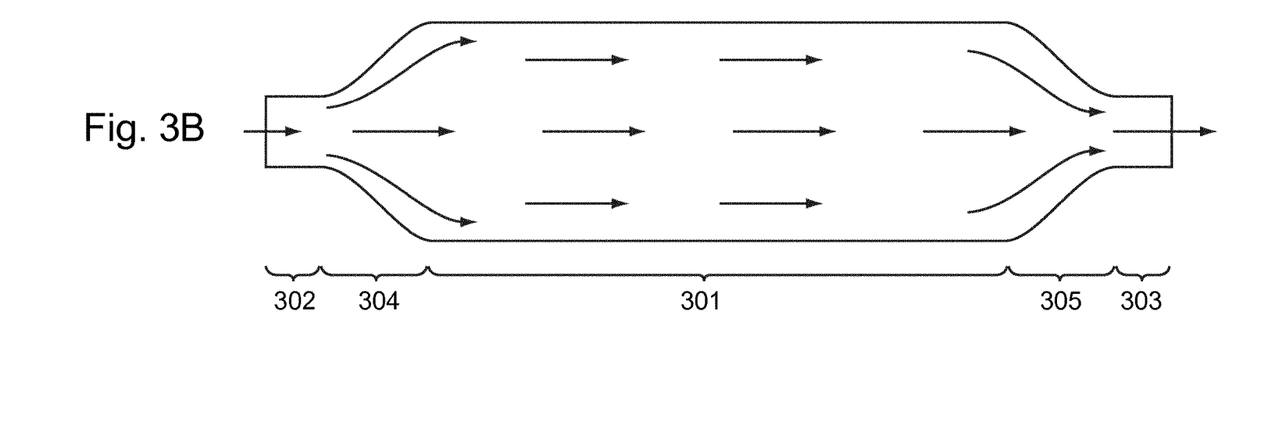
FIG. 3B is a schematic representation of a section of the irradiation chamber of FIG. 4, in which the streamlines of a liquid flowing in the irradiation chamber are schematically represented.

FIG. 3A is a schematic representation of an irradiation chamber 300 according to an embodiment of the invention. It is especially designed for a small purification apparatus such as a potable water fountain.

The irradiation chamber 300 has a main portion 301 which is substantially cylindrical, an inlet portion 302 and an outlet portion 303. Compared to the irradiation chamber of FIG. 1, the inlet potion 302 and the outlet portion 303 of the irradiation chamber represented in FIG. 3 are connected to the main portion 301 by smoothly curved, rounded, connecting portions 304, 305.

In particular, the connecting portions 304, 305 have a progressive change in their respective concavity. This results in an irradiation chamber defining a cavity having an internal surface having no sharp edge which forms a recess or a corner. The internal surface of the irradiation chamber defines its internal volume, in which the liquid to be disinfected flows. In a general manner, the irradiation chamber according to any embodiment of the invention defines a cavity having a rounded internal surface having smooth changes of concavity.

In a particular embodiment of the invention, the surface of the cavity defined by the irradiation chamber is a surface of revolution. There is no cusp along the generatrix of this surface of revolution. In other word, the mathematical function which defines generatrix of this surface of revolution is differentiable all along the part of the curve defining the surface.

Because there is no recess in the internal surface of the irradiation chamber, inorganic deposits are prevented. A liquid crossing the irradiation chamber flows in the whole volume of the irradiation chamber. There is no significant dead volume, or, at least, the dead volumes are strongly limited.

Figure 4:
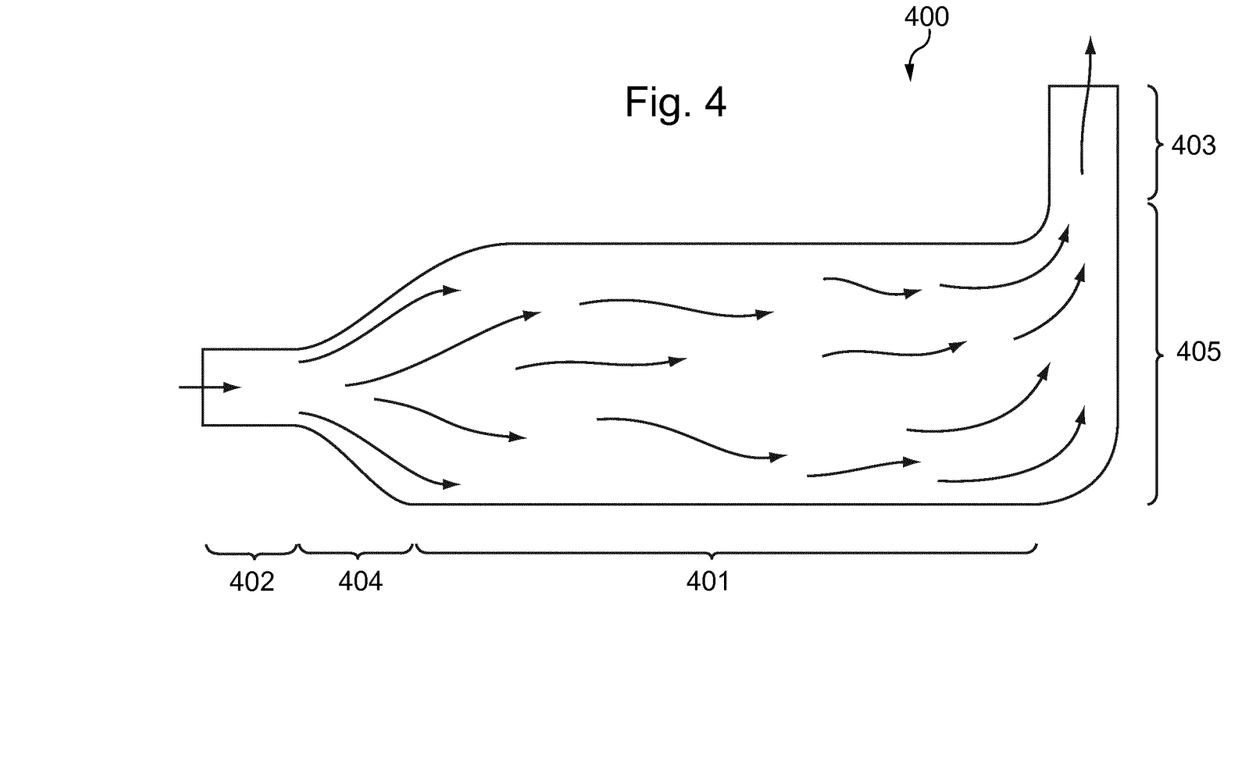
FIG. 4 is a schematic representation of a section of the irradiation chamber according to another embodiment of the invention.

FIG. 4 shows a schematic representation of a section of the irradiation chamber according to another embodiment of the invention. In this embodiment, the irradiation chamber 400 has a main portion 401 which is substantially cylindrical, an inlet portion 402 and an outlet portion 403. The outlet portion is substantially orthogonal to the inlet portion. The irradiation chamber and the cavity that it defines is thus L-shaped. Of course, any angle value may be formed between the inlet portion 402 and the outlet portion 403 without departing from the invention.

As in the embodiment of the invention shown in FIG. 3, the inlet potion 402 is connected to the main portion 401 by smooth, rounded, first connecting portion 404. The second connecting portion 405 connecting the main portion 401 to the outlet portion 403 is an elbow. The so formed elbow is preferably as large and rounded as possible.

As shown in the above-described embodiment of the invention, an irradiation chamber according to the invention has an internal surface having no edge forming a corner.

Many configurations are possible. The irradiation chamber has an elongated shape, for an easier positioning of the ultraviolet light emitting means and an enhanced irradiation time of the liquid flowing in the irradiation chamber. The light ultraviolet light emitting means are, in a general manner, means able to irradiate ultraviolet light in the irradiation chamber. The light ultraviolet light emitting means may comprise for example ultraviolet light emitting diodes (UV-LEDs) or optical fiber portions connected to at least one ultraviolet light source which are configured to transmit ultraviolet light in the irradiation chamber. The main portion may have a substantially cylindrical shape with a circular section. It may have in other embodiments an oval section, or other elongated shapes. The section of the main portion may be constant, i.e. it may have the same shape and size along the main portion, or evolve along the main portion. In other embodiments (not represented), the main portion of the irradiation chamber may itself be bent, e.g. being L-shaped or U-shaped, with a rounded elbow between the branches of said main portion.

The typical volume of an irradiation chamber for small purification apparatuses is under 200 mL, e.g. around 100 mL. If the irradiation chamber has an elongated shape, its length may be around 10 cm. If the internal cross section of the main portion of the irradiation chamber is constant along its length, the cross section may have a surface typically comprised 0.5 cm$^2$ and 4 cm$^2$. If the cross section is circular (the main part is a revolution cylinder) its diameter may be comprised for example between 1 cm and 2 cm.

It must be appreciated that these values are only typical orders of magnitude which do not limit the scope of the invention.

In any embodiment of the invention, the connecting portion may be shaped so that they do not comprise any curved surface having a radius of curvature under 0.5 cm. In an embodiment of the invention where the main portion of the irradiation chamber is a cylinder of revolution, the connecting portion may typically be shaped so that they do not comprise any curved surface having a radius of curvature under the radius of the cylinder forming the main portion.

The absence of angles or corners in the irradiation chamber makes possible to avoid the stagnation of water in said chamber. The water flows through the chamber and the streamlines follow the rounded shape of the chamber. This rounded shape makes possible to prevent an excessive development of bacteria, the formation of a biofilm, and inorganic deposit in the irradiation chamber.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. An irradiation chamber for a liquid purification apparatus using ultraviolet light irradiation against reproduction of pathogenic microorganisms, the irradiation chamber comprising an inlet portion, an outlet portion, and a main portion having an elongated shape comprising a cylindrical part having a volume of 200 mL or less, the main portion connected to the inlet portion and the outlet portion by smoothly curved connecting portions each composed of curved surfaces having a curvature radius greater than or equal to a radius of the cylindrical part and greater than or equal to 0.5 cm, the irradiation chamber having an internal surface defining a cavity, the irradiation chamber comprising an ultraviolet light emitting member configured to irradiate a liquid in the irradiation chamber with ultraviolet light, the main portion having a shape enlarged compared to the inlet portion, and the internal surface of the irradiation chamber defining the cavity is a three dimensional rounded surface having no edge which forms a recess.

2. The irradiation chamber according to claim 1, wherein the internal surface of the irradiation chamber defining the cavity is a surface of revolution whose generatrix is a portion of a curve having no cusp all along the portion of the curve.

3. The irradiation chamber according to claim 1, wherein the main portion of the irradiation chamber has a length between 5 cm and 15 cm inclusive.

4. The irradiation chamber according to claim 1, wherein the main portion of the irradiation chamber has an internal constant cross section having a surface area between 0.5 cm$^2$ and 4 cm$^2$ inclusive.

5. The irradiation chamber according to claim 1, wherein the outlet portion is collinear to the inlet portion.

6. The irradiation chamber according to claim 1, wherein the outlet portion is substantially orthogonal with the inlet portion.

7. The irradiation chamber according to claim 1, wherein the ultraviolet light emitting member comprises ultraviolet light emitting diodes.

8. The irradiation chamber according to claim 1, wherein the ultraviolet light emitting member comprises optical fiber portions which are connected to at least one ultraviolet light source and which are configured to transmit ultraviolet light from said at least one source into the irradiation chamber.

9. A liquid purification apparatus comprising an irradiation chamber using ultraviolet light irradiation against the reproduction of pathogenic microorganisms, the irradiation chamber comprising an inlet portion, an outlet portion, and a main portion having an elongated shape comprising a cylindrical part having a volume of 200 mL or less, the main portion connected to the inlet portion and the outlet portion by smoothly curved connecting portions each composed of curved surfaces having a curvature radius greater than or equal to a radius of the cylindrical part and greater than or equal to 0.5 cm, the irradiation chamber having an internal surface defining a cavity, the irradiation chamber comprising an ultraviolet light emitting member configured to irradiate a liquid in the irradiation chamber with ultraviolet light, the main portion having a shape enlarged compared to the inlet portion, and the internal surface of the irradiation chamber defining the cavity is a three dimensional rounded surface having no edge which forms a recess.

10. The liquid purification apparatus according to claim 9, wherein the internal surface of the irradiation chamber defining the cavity is a surface of revolution whose generatrix is a portion of a curve having no cusp all along the portion of the curve.

11. The liquid purification apparatus according to claim 9, wherein the main portion of the irradiation chamber has a length between 5 cm and 15 cm inclusive.

12. The liquid purification apparatus according to claim 9, wherein the main portion of the irradiation chamber has an internal constant cross section having a surface area between 0.5 cm$^2$ and 4 cm$^2$ inclusive.

13. The liquid purification apparatus according to claim 9, wherein the outlet portion is collinear to the inlet portion.

14. The liquid purification apparatus according to claim 9, wherein the ultraviolet light emitting member comprises ultraviolet light emitting diodes.

15. A beverage dispenser comprising a liquid purification apparatus comprising an irradiation chamber using ultraviolet light irradiation against the reproduction of pathogenic microorganisms, the irradiation chamber comprising an inlet portion, an outlet portion, and a main portion having an elongated shape comprising a cylindrical part having a volume of 200 mL or less, the main portion connected to the inlet portion and the outlet portion by smoothly curved connecting portions each composed of curved surfaces having a curvature radius greater than or equal to a radius of the cylindrical part and greater than or equal to 0.5 cm, the irradiation chamber having an internal surface defining a cavity, the irradiation chamber comprising an ultraviolet light emitting member configured to irradiate a liquid in the irradiation chamber with ultraviolet light, the main portion having a shape enlarged compared to the inlet portion, and the internal surface of the irradiation chamber defining the cavity is a three dimensional rounded surface, having no edge which forms a recess, the main portion configured to purify a beverage by ultraviolet irradiation before delivery of the beverage.

16. The beverage dispenser according to claim 15, wherein the internal surface of the irradiation chamber defining the cavity is a surface of revolution whose generatrix is a portion of a curve having no cusp all along the portion of the curve.

17. The beverage dispenser according to claim 15, wherein the main portion of the irradiation chamber has a length between 5 cm and 15 cm inclusive.

18. The beverage dispenser according to claim 15, wherein the main portion of the irradiation chamber has an internal constant cross section having a surface area between 0.5 cm$^2$ and 4 cm$^2$ inclusive.

19. The beverage dispenser according to claim 15, wherein the outlet portion is collinear to the inlet portion.

20. The beverage dispenser according to claim 15, wherein the ultraviolet light emitting member comprises ultraviolet light emitting diodes.

* * * * *